US008103065B2

(12) United States Patent
Richardson

(10) Patent No.: US 8,103,065 B2
(45) Date of Patent: Jan. 24, 2012

(54) ASSESSMENT OF MEDICAL CONDITIONS

(75) Inventor: Charles Richardson, Monroe, NC (US)

(73) Assignee: LifeScience Solutions LLC, Charlotte, NC (US)

(*) Notice: Subject to any disclaimer, the term of this patent is extended or adjusted under 35 U.S.C. 154(b) by 1492 days.

(21) Appl. No.: 11/326,091

(22) Filed: Jan. 5, 2006

(65) Prior Publication Data
US 2007/0156030 A1 Jul. 5, 2007

(51) Int. Cl.
G06K 9/00 (2006.01)
G06K 9/44 (2006.01)

(52) U.S. Cl. ......... 382/128; 382/100; 128/920; 600/509

(58) Field of Classification Search .................. 382/100, 382/128; 128/920; 600/509, 516, 517
See application file for complete search history.

(56) References Cited

U.S. PATENT DOCUMENTS

| | | |
|---|---|---|
| 3,302,639 A | 2/1967 | Koffler |
| 3,523,539 A | 8/1970 | Lavezzo et al. |
| 3,662,758 A | 5/1972 | Glover |
| 3,669,120 A | 6/1972 | Nielsen |
| 3,835,865 A | 9/1974 | Bowers |
| 3,925,041 A | 12/1975 | Patterson et al. |
| 3,985,142 A | 10/1976 | Wickham |
| 4,114,627 A | 9/1978 | Lewyn et al. |
| 4,531,527 A | 7/1985 | Reinhold et al. |
| 4,821,724 A | 4/1989 | Whigham et al. |
| 5,139,028 A | 8/1992 | Steinhaus et al. |
| 5,139,668 A | 8/1992 | Pan et al. |
| 5,161,540 A | 11/1992 | Mueller |
| 5,188,116 A * | 2/1993 | Pommrehn et al. ........... 600/509 |
| 5,197,480 A | 3/1993 | Gebhardt |
| 5,246,008 A | 9/1993 | Mueller |
| 5,411,031 A | 5/1995 | Yomtov |
| 5,758,654 A * | 6/1998 | Burton-Krahn et al. ...... 600/517 |
| 5,782,890 A | 7/1998 | Wahlstrand et al. |
| 5,820,659 A | 10/1998 | Ekiner et al. |
| 5,833,623 A | 11/1998 | Mann et al. |
| 6,044,294 A | 3/2000 | Mortazavi et al. |
| 6,198,965 B1 | 3/2001 | Penner et al. |
| 6,234,973 B1 | 5/2001 | Meador et al. |

(Continued)

FOREIGN PATENT DOCUMENTS

WO WO 2008/029362 A1 3/2008

OTHER PUBLICATIONS

Jager, F. et al., *Detection of Transient ST Segment Episodes During Ambulatory ECG Monitoring*, Computers and Biomedical Research 31, Article No. CO981483, (1998), pp. 305-322.

(Continued)

*Primary Examiner* — Jason M Repko
*Assistant Examiner* — Patrick Edwards
(74) *Attorney, Agent, or Firm* — Alston & Bird LLP

(57) ABSTRACT

The present invention is directed to methods for analyzing electrical signals generated by biological tissues, such as muscles (e.g., cardiac or skeletal muscle) and tissue within the nervous system (e.g., neurons within the central and peripheral nervous systems). The tissue may be a patient's own, or it may have been transplanted into the patient from a donor organism or from a tissue or cell culture. The result of the analysis indicates the condition of the tissue, and results obtained over time can alert a patient or health care professional to changes in that condition.

27 Claims, 5 Drawing Sheets

U.S. PATENT DOCUMENTS

| | | |
|---|---|---|
| 6,269,264 B1 | 7/2001 | Weyant et al. |
| 6,411,840 B1 | 6/2002 | Bardy |
| 6,473,638 B2 | 10/2002 | Ferek-Petric |
| 6,740,636 B2 | 5/2004 | Horuk |
| 6,745,076 B2 | 6/2004 | Wohlgemuth et al. |
| 6,824,592 B2 | 11/2004 | Monzyk et al. |
| 6,983,183 B2 * | 1/2006 | Thiagarajan et al. ......... 600/509 |
| 7,277,754 B2 | 10/2007 | McCabe et al. |
| 7,565,193 B2 * | 7/2009 | Laken ........................... 600/544 |
| 7,567,836 B2 * | 7/2009 | Zhang ........................... 600/512 |
| 2003/0158466 A1 | 8/2003 | Lynn et al. |
| 2003/0163057 A1 | 8/2003 | Flick et al. |
| 2005/0027323 A1 | 2/2005 | Mulligan et al. |
| 2005/0113703 A1 | 5/2005 | Farringdon et al. |
| 2005/0234360 A1 | 10/2005 | Richardson |
| 2007/0062870 A1 | 3/2007 | Chen et al. |
| 2007/0156030 A1 | 7/2007 | Richardson |
| 2007/0179392 A1 | 8/2007 | Zhang |
| 2007/0191722 A1 | 8/2007 | Richardson |

OTHER PUBLICATIONS

Michaelides, A. P. et al., *New Coronary Artery Disease Index Based on Exercise-Induced QRS Changes*, American Heart Journal, (Aug. 1990), pp. 292-302.

Toth, A. et al., *QRS Score: A Composite Index of Exercise-Induced Changes in the Q, R, and S Waves During Exercise Stress Testing in Patients With Ischemic Heart Disease*, A.N.E., vol. 6, No. 4, (Oct. 2001), pp. 310-318.

Search Report for European Application EP 07 76 3049 mailed May 12, 2010.

* cited by examiner

Calculate the Green Areas for
Total Area Under Curve Template

ASSESSMENT OF MEDICAL CONDITIONS

TECHNICAL FIELD

The present invention relates to systems, methods, and computer programs that can be used to monitor a medical condition. More specifically, the products and processes can be used to detect a change in a biological tissue by assessing activity, such as electrical activity, within the tissue.

BACKGROUND

Electrocardiography is a common, painless medical technique that records the electrical activity of the heart as an electrocardiogram or ECG (also referred to as an EKG). The resulting waveform is a graphical representation of the electrical activity of the heart as a function of time. The waveform may be viewed on a monitor or printed on a material, usually paper, which is commonly referred to as an "ECG strip". From an analysis of the ECG strip, various physical and biological properties of the heart may be determined or estimated. For example, one can assess the rate at which electrical impulses are moving through the heart and the rate and regularity of heartbeats. An analysis of the waveform can also reveal signs of damage to the heart or indicate problems with the electrical conduction system.

SUMMARY

The present invention is based, in part, on our discovery of methods that can be used to analyze the electrical signals generated by biological tissues such as muscles and tissue within the nervous system. The result of the analysis indicates the condition of the tissue, or a particular aspect thereof, and results obtained over time can alert a patient or health care professional to changes in that condition. Generally, the methods are carried out by obtaining a recording of electrical activity that includes multiple signaling events (e.g., periodic waveforms representative of the electrical activity), selecting one or more features of an event (e.g., its amplitude or frequency), and calculating an average value representing that event over a given number of selected multiples (e.g., 2-500 (e.g., 100-200)). The calculation can be, for example, a calculation of an area under a curve or a defined portion of a curve, a frequency difference between first and second points, which may each be within consecutive events, an ascending slope from a nadir to an apex or a defined portion between the nadir and apex, a descending slope from an apex to a nadir or a defined portion between the apex and nadir, or a difference in amplitude between an apex and a nadir.

We may refer to the recording of electrical activity obtained at a first point in time as the "baseline recording," and to the average result of a first calculation performed on a multiple of events within the baseline recording as the "first baseline template" (a second calculation giving rise to a second baseline template; a third calculation giving rise to a third baseline template; and so forth). The same process, or a substantially equivalent process, can be carried out on a recording of electrical activity obtained at a second and later point in time. We may refer to the recording obtained at the second point in time as the "captured recording," and to the average result of a first calculation performed on a multiple of events within the captured recording as the "first captured template" (a second calculation giving rise to a second captured template; a third calculation giving rise to a third captured template; and so forth). Once a baseline and corresponding captured template have been obtained, one would then calculate the variance between them. Where more than one feature is analyzed, giving rise to a second set of templates, we may refer to a second variance (i.e., the variance between the second baseline template and the second captured template); a third variance; a fourth variance; and so forth.

As some features of the signaling events may be more indicative of the condition of the tissue than others, various embodiments (e.g., the systems, methods, and computer programs of the invention) can also include a step in which the variances are scaled or weighted. For example, where two features of a signaling event are analyzed, one can scale first and second variances by first and second weighting factors. The sum of the first and second scaled variances can then be calculated. The calculated sum represents a difference between the baseline and captured templates that indicates a change in the condition of the tissue over time within the same patient. The calculated result from the baseline template can be compared to the calculated result from the captured template, a difference indicating a change in the condition of the tissue.

Accordingly, in a specific embodiment, the invention features a method for assessing a medical condition by: (1) obtaining a first baseline template corresponding to an average of results of a first calculation performed on a multiple of events within a first electrical signal acquired at a first time; (2) obtaining a first captured template corresponding to an average of results of the first calculation performed on a multiple of events within a second electrical signal acquired at a second time, which is later than the first time; (3) obtaining a second baseline template corresponding to an average of results of a second calculation performed on a multiple of events within the first electrical signal; (4) obtaining a second captured template corresponding to an average of results of the second calculation performed on a multiple of events within the second electrical signal; (5) calculating a first variance between the first baseline and captured templates; (6) calculating a second variance between the second baseline and captured templates; (7) optionally, scaling the first and second variances by first and second weighting factors, respectively, to produce first and second scaled variances; and (8) calculating a first sum of the first and second variances or, if scaled, of the scaled variances.

Where the first sum indicates that the variance between the baseline and captured templates is about 5-10%, the patient and/or a member of their health care team would be alerted that there is a change in the condition of the tissue that merits close observation and, if advisable, intervention. Intervention may be appropriate, for example, in view of the patient's overall medical condition and/or where other diagnostic tests or subjective input from the patient indicates as much. Accordingly, the methods, systems, and programs of the invention can include providing and assessing data obtained from the patient (e.g., by way of a questionaire or interview) or other diagnostic tests. Where the first sum indicates that the variance between the baseline and captured templates is about 10-15%, the patient and/or a member of their health care team would be alerted that there is a substantial and probably seriously detrimental change in the condition of the tissue. For example, where the tissue being monitored is a transplanted heart, a variance of 10-15% (or more) indicates that the heart is in the process of rejection.

The teaching above assumes that the change in the electrical activity within the tissue is detrimental; that one or more of the features of the captured template are less desirable than those of the baseline template. The methods, systems, and programs of the invention may also reveal, however, an improvement or stabilization of a medical condition. For example, where one or more of the baseline templates are obtained from a healthy subject, a decrease in the variance between one or more of the baseline templates and one or more of the corresponding captured templates would indicate an improvement in the patient from whom the captured template was obtained. For example, a baseline template can be calculated based on a recording obtained from the patient being evaluated at an earlier time when the patient was in better health or from another patient or group of patients who are healthy or who have responded positively to a treatment or procedure.

Thus, whether the outcome indicates a detrimental, beneficial, or minimal change in a given patient's condition, one can generate or obtain threshold values that are indicative of a medical condition of interest. For example, one can obtain one or more baseline templates from a patient or group of patients having a particular medical condition. For example, the patient may be one who has received a heart or heart-lung transplant and who exhibits few, if any, signs of rejection after a certain period of time (e.g., a week after the transplantation). In other instances, the patient may be one who has been diagnosed with a neurodegenerative disease (e.g., multiple sclerosis) that is in an early stage or who that has reached an advanced stage. In each instance, one can generate a baseline template from a patient of interest and compare this template to a captured template generated from the patient. Thus, the systems, methods, and computer programs of the present invention can be configured to assess a given patient over time or to assess a given patient at any point in time relative to a threshold value representing a population of patients having a particular condition. In either event, the systems, methods, and computer programs can be used to assess the efficacy of a treatment. For example, if a given sum indicates that the condition of a patient's tissue is deteriorating over time, or that it is inferior to that observed in a desirable patient pool, one can administer a therapeutic regime (e.g., a drug or physical therapy) and repeat the comparative process. If the deterioration slows or the patient's condition approaches that observed in the desirable pool, one can conclude that the therapeutic regime is effective or is having a positive effect on the patient's medical condition.

Electrical signals can be acquired from biological tissues by any means known in the art. For example, first and second electrical signals can be acquired from first and second electrocardiograms; first and second electromyograms (EMGs or simply "myograms"); or first and second electroencephalograms (EEGs). The means for acquiring the electrical signal can be selected on the basis of the medical condition being assessed. For example, while the invention is not so limited, one can use an electrocardiogram to assess heart failure and an electromyogram and/or electroencephalogram to assess neurodegenerative disease, brain damage (whether congenital or caused by trauma, substance abuse, or a disease such as Parkinson's Disease, Huntington's Disease, or Alzheimer's Disease), or other conditions. For example, the systems, methods, and computer programs described herein can be used to assess a patient who has, or who has been diagnosed as having, polymyositis, a denervated tissue (resulting, for example, from trauma), carpal tunnel syndrome, amyotrophic lateral sclerosis (ALS), muscular dystrophy, myasthenia gravis, alcoholic neuropathy, axillary nerve dysfunction, Becker's muscular dystrophy, brachial plexopathy, cervical spondylosis, dermatomyositis, Duchenne muscular dystrophy, Friedreich's ataxia, or Shy-Drager syndrome. An electromyogram can be used where, for example, a neurodegenerative disease causes a motor disorder. While certain methods of detecting an electrical signal provide the advantage of being non-invasive (e.g., an electrocardiogram), the invention is not so limited. Electrical signals can also be detected and transmitted by devices that are wholly or partially implanted within the patient's body.

Optionally, the systems, methods, and computer programs can exclude results of the first calculation that are greater than a first predetermined value and that are less than a second predetermined value from the average of results of the first calculation. The first predetermined value can be the sum of a mean and a standard deviation of the results of the first calculation and the second predetermined value can be the difference between the mean and the standard deviation. For example, averaging using standard deviation calculations that eliminate the top 5% and bottom 5% of the template calculations can compensate for miscellaneous anomalies. Greater or lesser percentages may be used depending upon the anomaly (e.g., one can eliminate 1%, 2%, 3%, or 4% of the top and bottom template calculations where that minimal correction neutralizes the anomaly or more than 5% of the top and bottom template calculation (e.g., 6, 8, 10, or 12%) where that extent is required for correction).

The details of one or more embodiments of the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

The present invention is directed to methods for analyzing electrical signals generated by biological tissues, such as muscles (e.g., cardiac or skeletal muscle) and tissue within the nervous system (e.g., neurons within the central and peripheral nervous systems). The tissue may be a patient's own, or it may have been transplanted into the patient from a donor organism or from a tissue or cell culture. The result of the analysis indicates the condition of the tissue, and results obtained over time can alert a patient or health care professional to changes in that condition.

Figure 1:
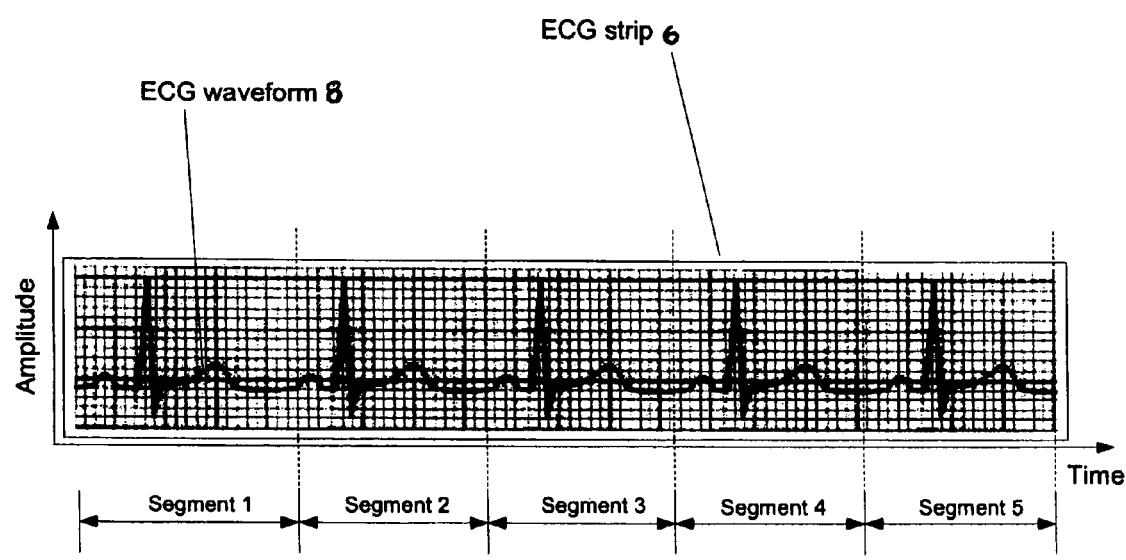
FIG. 1 shows an exemplary ECG strip of a normal heartbeat.

FIG. 1 shows a sample ECG strip 6 from a normal heart. The ECG strip 6 includes a printed waveform 8 having an amplitude that varies with time. The waveform 8 is divided into segments (e.g., segments 1-5) that each correspond to the electrical activity measured over an individual heart beat. From an analysis of the waveform 8, various physical and biological properties of the heart may be determined and/or estimated. Examples of these include the rate of movement of the heart's electrical impulses, the rate and regularity of heartbeats, and the size and position of the chambers of the heart. Based on the physical and biological properties measured from the waveform 8 and/or from a direct analysis of the waveform 8, itself, a skilled practitioner can determine if the heart is operating normally. An analysis of the waveform 8 can also reveal signs of damage to the heart; reveal problems with the electrical conduction system; assist in diagnosing a disease (e.g., heart failure); and monitor the effects of drugs or devices such as pacemakers and implantable cardioverter defibrillators (ICDs).

Figure 2:
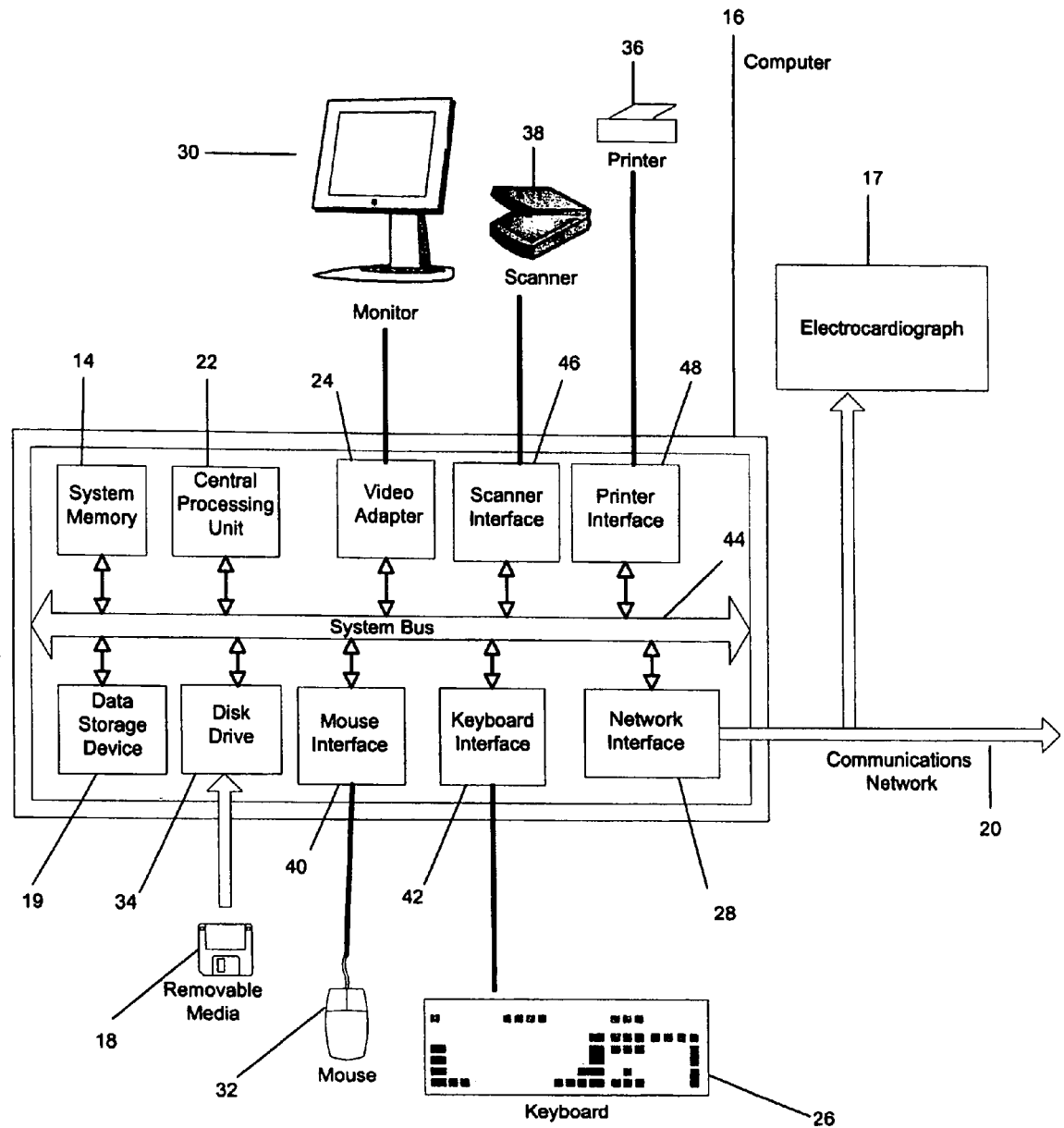
FIG. 2 shows a block diagram of a system for acquiring and analyzing ECG recordings.

FIG. 2 shows an exemplary data acquisition and processing system 10 for acquiring data indicative of electrical activity within a patient's body (e.g., from the tissues described herein) and for analyzing the data to assess a medical condition associated with the patient's tissue. Examples of such tissue include heart, muscle, brain, and other electrically active tissues. The system 10 includes medical data acquisition equipment 17 that measures electrical activity of a patient's tissue (e.g., equipment for electrocardiograph) and encodes the acquired data as a recording from which a graphical representation of the data can be generated. An example of a graphical representation is a waveform having an amplitude that varies with time. The waveform may be divided into segments that each corresponds to electrical activity measured before, during, or after an occurrence of a biological event affecting the tissue (e.g., a heart beat measured before, during, or after the administration of a medication or exposure to a stressor). In some embodiments, the recording is an electronic file that includes a list of coordinates from which waveforms can be plotted using a graphing application such as Excel® available from Microsoft Inc.

Examples of equipment 17 include, but are not limited to, equipment for performing electrocardiography, electromyography, or electroencephalography. The equipment generates, respectively, ECGs, electromyographs (EMGs) and electroencephalographs (EEGs).

The system 10 also includes a computer 16 for analyzing recordings produced by the equipment 17; a monitor 30 for displaying data, such as a waveform, to a skilled practitioner; and a keyboard 26 coupled to the computer 16 by a wired or a wireless link. The computer 16 is coupled to a pointing device 32 for controlling an on-screen element, such as a pointer icon or cursor, presented on the monitor 30. The pointing device 32 may be implemented using a track ball, a joy stick, touch sensitive tablet or screen, track path, or, as illustrated, a mouse.

The computer 16 includes a data storage device 19, such as a hard drive, for storing data; system memory 14 for storing computer readable instructions, which can be in the form of software; and a central processing unit (CPU) 22 for executing the software stored in the system memory 14. The CPU 22 fetches, decodes, and executes instructions, and transfers information to and from other resources via the system bus 44, the computer's 16 main data-transfer path. The system bus 44 provides a medium for the exchange of data between the system memory 14, the CPU 22, and other components within the computer 16.

Software may be loaded into the system memory 14 from removable media 18 such as a floppy disk, CD-ROM, or other storage mechanism capable of loading software into the system memory 14. The system memory 14, coupled to the system bus 44, includes random access memory (RAM), read only memory (ROM), and other forms of volatile and non-volatile memory. The system memory 14 also includes circuitry that allows information to be stored and retrieved by the CPU 22. The computer 16 also includes a video adapter 24 that interfaces with the monitor 30, peripheral device interfaces, such as a mouse and keyboard interface 26, disk drives 34 for reading from and writing to the removable media 18, such as a floppy disk drive, or a CD-ROM drive, and a network interface 28. The disk drive 34 includes special purpose integrated circuits and associated circuitry that directs and controls the transfer of data to and from the removable media 18. The keyboard and mouse interfaces 40 and 42, respectively, interface with the keyboard 26 and the pointing device 32.

The computer 16 may include one or more peripheral devices, such a network interface 28 and a disk drive 34, each of which may be internal or external to the enclosure of the computer 16. The disk drive 34 may be any device capable of reading and writing to the machine readable medium 18. Examples of the disk drive 34 include magnetic disk drives and optical disk drives. An output device such as a printer 36 and an input device such as a scanner 38 may also be coupled to the computer 16.

The monitor 30, which is controlled by a video adapter 24, is used to display visual output generated by the computer 16. Such visual output may include text, graphics, animated graphics, and video. The monitor 30 may be implemented, for example, with a CRT-based video display, an LCD-based flat panel display, or a gas plasma-based flat-panel display. The video adapter 24 includes electronic components required to generate a video signal that is sent to the monitor 30.

The printer 36 is coupled to the computer via a printer interface 48. Examples of a printer interface include a parallel port and a serial port. The printer 36 is used to print text or a computer-generated image (or combinations thereof) on paper or on another medium, such as a transparency sheet. Other types of printers may include an image setter, a plotter, or a film recorder.

The scanner 38 is coupled to the computer 16 via the scanner interface 46. Examples of the scanner interface 46 include a parallel port and a serial port. The scanner 38 is used to convert text and/or images from paper to an electronic file.

The system 10 includes communications network 20 for sending data from the equipment 17 to the computer 16. Communication between the computer 16 and the equipment 17 over the network 20 may be facilitated by the network interface 28. In some embodiments, the network 20 is simply a cable connecting the computer 16 to the equipment 17, and the network interface 28 is a port that controls the transmission of information between the computer 16 and the equipment 17 according to a communication standard. Examples of ports include serial ports, universal serial bus (USB) ports, and parallel ports. The transmissions over the communications network 20 can be synchronous (controlled by some standard such as a clock) or asynchronous (managed by the exchange of control signals that govern the flow of information).

In other embodiments, the communications network 20 includes one or more of a local area network (LAN), a larger group of interconnected systems such as the internet, a private intranet, and other similar wired or wireless networks. Additionally, the network 20 may provide distributed processing, which involves several computers in the sharing of workloads or cooperative efforts in performing a task. The communications network 20 can also connect to other systems. In some exemplary embodiments, the network 20 supports multiple users collaborating on the analysis of recordings obtained from the equipment 17. In these embodiments, recordings and analyses thereof may be transmitted between users at computers akin to computer 16 over the network 20. In some embodiments, the printer 36, the scanner 38, or both are coupled to the computer via the communications network 22.

After a recording is generated by the equipment 17, it is transmitted to the computer 16 and stored in data storage device 19. In some embodiments, removable media 18 on which the recording is stored delivers the recording to the computer 16. In these embodiments, the disk drive 34 extracts the recording from the removable media 18 and the system bus 44 moves it to the data storage device 19. In other embodiments, the communications network 20 delivers the recording from the equipment 17 to the computer 16. In further embodiments, the scanner 38 converts a physical representation generated from the recording, such as a strip of paper on which waveforms are printed, into an electronic file that includes the data stored in the original recording. The electronic file may then be stored in the data storage device 19. After the recording from the equipment 17 is loaded into the computer 16, the CPU 22 executes software stored within the system memory to generate the waveform.

Figure 3:
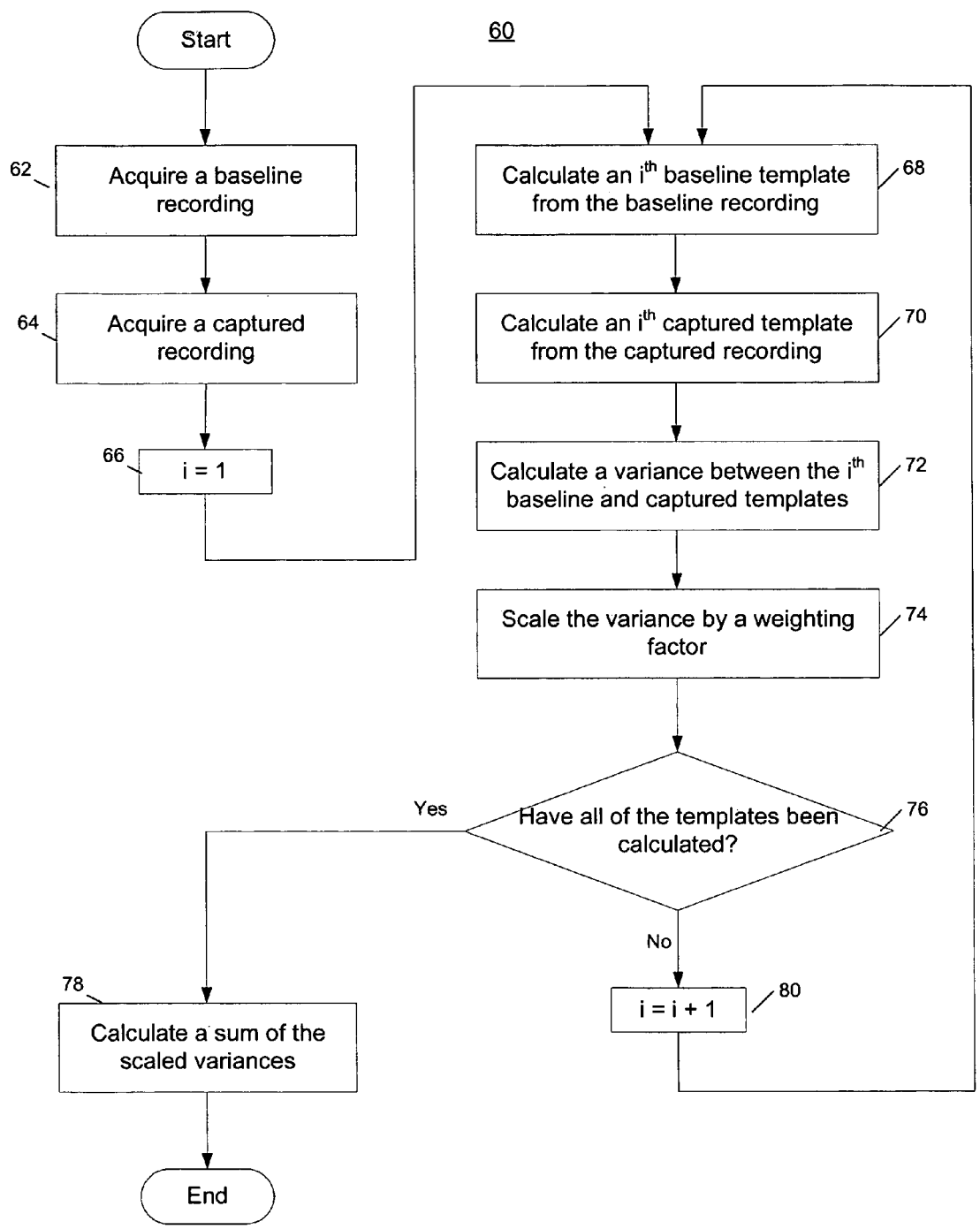
FIG. 3 shows a flowchart of a comparative process for analyzing recordings obtained using the system shown in FIG. 2.

FIG. 3 illustrates a flowchart of a process 60 by which the system 10 assesses a medical condition of a biological tissue from which recordings of electrical activity are generated by the equipment 17. A baseline recording from the biological tissue is acquired (62) by the equipment 17 at a first time and sent to the computer 16, where it is stored in the data storage device 19. At a second time, which is later than the first time, a captured recording from the biological tissue is acquired (64) by the equipment 17, sent to the computer 16, and stored in the data storage device 19. The baseline recording may include several recordings acquired at multiple consecutive or non-consecutive times (e.g., three non-consecutive days within the same week). Likewise, the captured recording may include several recordings acquired at multiple times.

When a baseline recording is acquired from the patient, the state of the tissue may be known. In some embodiments, the baseline recording is acquired before the patient undergoes a method of treatment, such as surgery (e.g., heart transplant, pacemaker implantation, or coronary bypass surgery) or drug delivery (e.g., immunosuppressants, diuretics, β blockers, or non-steroidal anti-inflammatory agents) and the captured recording is acquired a prescribed time after the method of treatment has been performed. In other embodiments, the baseline recording is acquired shortly after the patient undergoes a method of treatment, and the captured template is acquired at a later time (e.g., one or more days, weeks, or months later). For example, a baseline recording of a patient who has undergone heart surgery may include several recordings acquired in the mornings and evenings of the initial week following the surgery.

After the baseline and captured recordings are acquired (62 and 64), the CPU 22 generates a baseline waveform from the baseline recording and captured waveform from the captured recording. The waveform may be divided into segments that each correspond to an event. For example, each of the baseline and captured waveforms may be divided into segments that each corresponds to an individual heartbeat. In some embodiments, each of the baseline and captured waveforms is divided into segments that number between about 100 and 200 (e.g., 95, 100, 110, 125, 150, 175, 200, 205).

An index i is set to one (step 66) and the first baseline template is calculated (68) based on a first type of calculation that computes one or more features of a segment of the baseline waveform or, in some cases, features of the baseline waveform, itself. Examples of such features include an area under a curve or a defined portion of a curve, a frequency difference between first and second points that within consecutive segments, an ascending slope from a nadir to an apex, a descending slope from an apex to a nadir, or a difference in amplitude between an apex and a nadir. Examples of these features are described in further detail with respect to FIGS. 4 and 5a-c in the context of a waveform generated by an ECG recording. The calculations are performed over a selected number of segments, which may include all of the segments of the baseline waveform or a subset of segments (e.g., the first 200 segments out of 500 segments total). In some embodiments in which the tissue being monitored is a transplanted heart, the calculations are performed for each heartbeat for the duration of the time the ECG monitors a number of heart beats (e.g., a number ranging between 100 and 200 heartbeats).

A statistical test is then performed on the results of the calculation to determine which, if any, results are statistically anomalous and, as a result, should be discarded. In some embodiments, the mean and standard deviation of the results are calculated and those results lying above or below the mean by an amount equal to a predetermined multiple of the standard deviation (e.g., twice the standard deviation, three times the standard deviation, or more) are discarded. In other embodiments, results lying within a predetermined percentage of the top and bottom range of results are discarded. For example, the top and bottom 5% of the results may be eliminated. Results may be discarded based on other statistical tests, such as a chi-square test or a student t-test. An average of the remaining results, referred to as a "first baseline template", is calculated (68).

Similar to the calculation of the first baseline template, a first captured template is calculated (70) by performing the first calculation on segments of the captured waveform generated from the captured recording after discarding those results that are statistically anomalous and averaging the remaining results.

A variance between the first baseline and captured templates is then calculated (72) and optionally normalized by dividing it by the first baseline template. Where the baseline and captured templates are obtained from a single patient over time, the variance is indicative of a change in the condition of the tissue over a time interval spanning the time at which the baseline recording was acquired and the time at which the captured recording was acquired. Where the baseline template is obtained from another patient (e.g., a healthy patient), the variance is indicative of the difference between the condition of the patient's tissue and that of a healthy patient (or any other reference standard). Changes or differences may be due to the presence of a medical condition (e.g., transplant rejection). The results may be influenced by other factors, such as the patient's emotional state. For example, variance can be affected by the patient being excited, agitated, or stressed.

In embodiments in which two features of the baseline and captured recordings are analyzed, the features may not provide equal indications of the condition of the tissue. In that event, the variance can be scaled or weighted (74) by a weighting factor that better quantifies the relative importance of the features. The weighting factor can be assigned by cardiologists and can be applied to the total recordings in order to prioritize the templates and to determine which variances are the most reliable indicators of the condition of the tissue. In some embodiments, the weighting factor assigned to the variance between the first baseline and captured templates is a value between zero and one, such that a sum of that weighting factor and all other weighting factors equates to one. In other embodiments, the weighting factor is expressed as a percentage (e.g., between zero and 100%). The process 60 determines (76) whether all of the templates have been calculated. If more templates are due to be calculated, the index i is incremented by one (80), and second baseline and captured templates are calculated (68 and 70) by averaging the results of a second type of calculation applied to segments of the baseline and captured waveforms generated from the baseline and captured recordings. A variance between the second baseline and captured templates is calculated (72) and the variance is then scaled (74) by a weighting factor. Until the process determines (76) that all of the templates have been calculated, the incrementing step (80), the calculation steps (68, 70, and 72) and the scaling step (74) are repeated. After all of the templates have been calculated, a sum of the scaled variances is calculated (78).

The sum may then be analyzed by a skilled practitioner or by software programs to assess one or more conditions of the tissue and/or patient. For example, a practitioner or software may determine that the sum indicates that the variance between the baseline and captured templates is within a given range that is indicative of the presence of an undesirable condition or an undesirable change in the condition of the tissue. In some examples, upon the computer 16 or a skilled practitioner determining that the sum indicates that the variance between the baseline and captured templates is about 5-10%, the computer 16 or a skilled practitioner alerts the patient and/or a member of their health care team that there is a change in the condition of the tissue that merits close observation and, if advisable in view of the patient's overall medical condition, recommends a course of intervention. In these examples, if the sum indicates that the variance between the baseline and captured templates is about 10-15%, the patient and/or a member of their health care team is alerted that there is a substantial and probably seriously detrimental change in the condition of the tissue (e.g., loss of functionality). In embodiments in which the tissue being monitored is a transplanted heart, a variance of 10-15% (or more), for example, indicates that the heart is in the process of rejection.

The sum may also be compared to predetermined threshold values that are indicative of the presence of a medical condition of interest if the sum is equal to or exceeded by that of the predetermined threshold value. For example, such threshold values may be determined based on data, such as baseline templates, obtained from a patient or group of patients having a medical condition similar to the condition being assessed in the patient of interest.

In some embodiments, the sum may be compared to one or more predetermined threshold values to assess the efficacy of a treatment by indicating an improvement in the condition of the tissue after the treatment has been administered to the patient. For example, if a given sum indicates that the condition of a patient's tissue is deteriorating over time, or that it is inferior to that observed in a desirable patient pool, one can administer a therapeutic regime (e.g., a drug or physical therapy) and repeat the comparative process 60. If the sum then indicates that the deterioration has slowed or that the patient's condition has approached that observed in the desirable pool, one can conclude that the therapeutic regime is effective.

Figure 4:
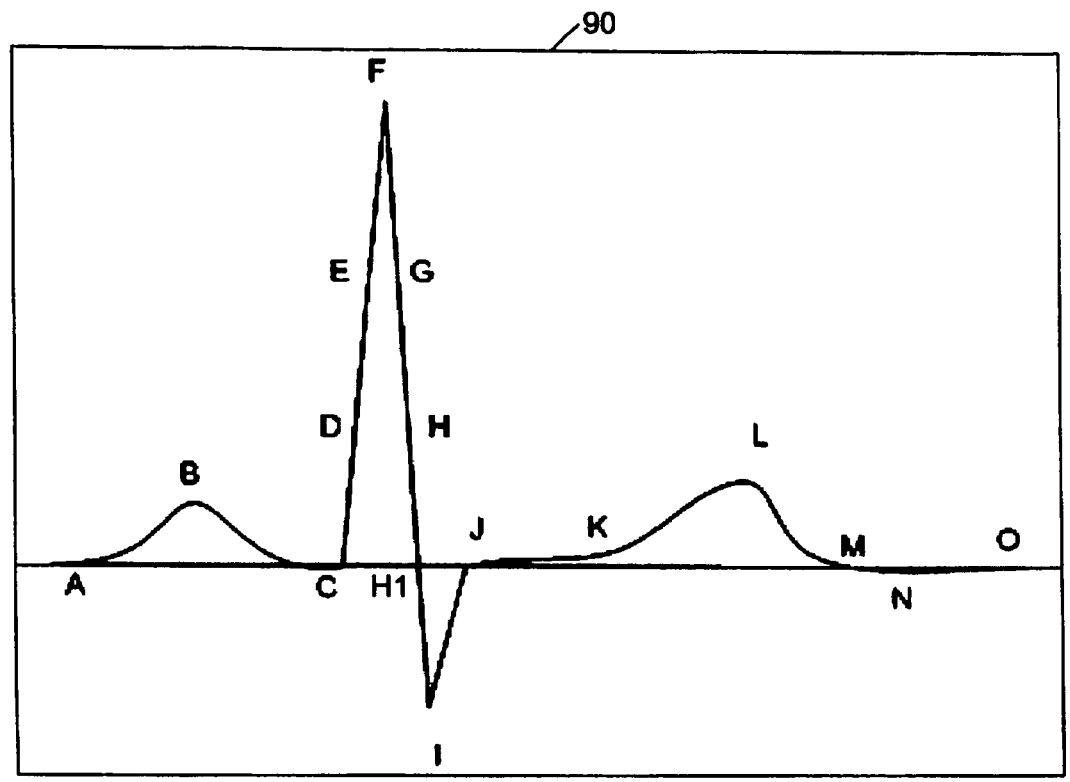
FIG. 4 shows a waveform from an ECG recording.

The following description with respect to FIGS. 4 and 5a-c describe particular embodiments directed to analyzing electrical activity of the heart and are not meant to be construed in a limiting sense. FIG. 4 shows a waveform segment 90 generated from an ECG recording of a patient's heart. The waveform segment 90 includes labeled points of interest that refer to industry standard points. The following table describes the labeled points in standard terminology.

TABLE

An explanation of points shown in FIG. 4

| Point Label | Explanation |
| --- | --- |
| A | Start of PR Interval |
| B | Apex of P Wave |
| C | Completion of PR, Start of QRS Interval |
| D | ⅓ point between baseline and F Point |
| E | ⅔ point between baseline and F Point |
| F | Apex of QRS Complex |
| G | ⅓ point between F Point and baseline |
| H | ⅔ point between F Point and baseline |
| I | Nadir of QRS Complex |
| J | J Point, End of QRS Interval, Start of ST Interval |
| K | End of ST Segment, Beginning of T Wave |
| L | Apex of T Wave |
| M | End of T Wave, Where Crosses baseline |
| N | Nadir of ST Interval |
| O | Point where back on baseline |

While the waveform segment 90 in FIG. 4 is indicative of "normal" cardiac activity over a given heartbeat, waveform segments corresponding to some beats can exhibit variations (e.g., more or fewer points at which the waveform segments cross the baseline per beat). Numerous calculations can be performed based on the various shapes within the waveform and the number of times the waveform crosses the baseline during the beat. Those calculations are still performed in the same manner as with the waveform segment 90 that is indicative of normal cardiac activity, but the calculations may be more numerous or include more variables. To calculate various features of the waveform segment 90, the software may break the waveform up into separate geometric areas defined by the points of interest.

Figure 5A:
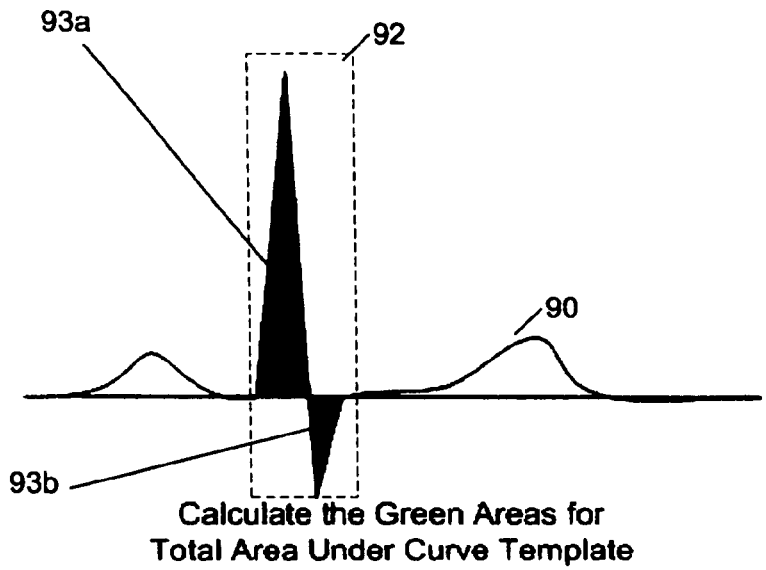
FIGS. 5a-c show graphical diagrams for use with calculating an area-under-the-curve template.

A first example of a feature that may be calculated at steps 68 and 70 of process 60 to yield baseline and captured templates is an area lying under a chosen portion of the waveform segment 90. The area to be used for the calculation is first identified. FIG. 5a shows the total area 92 that is calculated, depicted as shaded regions 93a and 93b. The calculated area 92 may then be used as the basis for the baseline and captured templates. The calculations for each of the areas 93a and 93b contributing to the total area 92 are based on geometric principles and performed by the computer 16. The calculation may become more complex as the waveform 90 exhibits more fluctuations and crossings over the baseline. As shown in FIG. 5a, there are two distinct areas, i.e., regions 93a and 93b, which require analysis and calculation. In some embodiments, fewer or more than two distinct areas may be determined.

The points of interest shown in FIG. 4 are generated along a linear timeline for each segment in a waveform. The duration of time between each of the points is a known value and may be constant or essentially constant. For example, the duration of time between each consecutive pair of points A-O may be a constant value (e.g., 1 ms, 5 ms, 10 ms, etc.). By having a linear valuation assigned to the points, a trapezoidal method for calculating the area under a curve can be used.

By using trapezoidal geometric principles, the total area under the curve 92, i.e., formed by points C through J, can be broken into four separate geometric shapes: two trapezoids and two triangles. The area 93a is bounded by points C through H1, where H1 refers to the point at which the line between points H and I cross the baseline. The area 93a may be divided into two trapezoids and one triangle, in which the first trapezoid is bounded by points C, D, H and H1; the second trapezoid is bounded by points D, E, G, and H; and the triangle is bounded by points E, F, and G. The area 93b is approximated as a triangle bounded by points H1, I, and J. Known formulas for calculating the areas of triangles and trapezoids are used to calculate the trapezoidal and triangular sections of areas 93a and 93b.

Figure 5B:
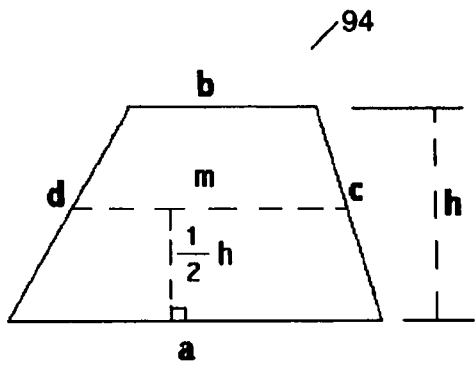

Referring to FIG. 5b, a diagram of a generic trapezoid 94 is shown. The trapezoid 94 has four sides a, b, c, and d, in which side a is parallel to side b; a height denoted by h; and a bisector m that cuts through the trapezoid 94 midway between sides a and b (i.e., at a distance equal to ½*h from each of the sides a and b) such that m=½(a+b). The area of the trapezoid 94 is given by the following equation:

$$\text{Area of Trapezoid} = \tfrac{1}{2} h^*(a+b) = m^*h. \quad \text{Equation 1}$$

Thus, according to Equation 1, the area of the first trapezoid, denoted $A_{trap\_1}$, that is defined by points C, D, H and H1 is the following:

$$A_{trap\_1} = \tfrac{1}{2}(D-C)^*((H-D)+(H1-C)). \quad \text{Equation 2}$$

Likewise, the area of the second trapezoid, denoted $A_{trap\_2}$, that is defined by points D, E, G, and H is the following:

$$A_{trap\_2} = \tfrac{1}{2}(E-D)^*((G-E)+(H-D)). \quad \text{Equation 3}$$

Figure 5C:
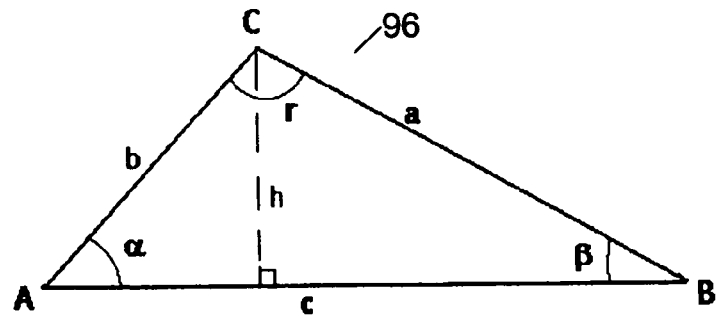

Referring to FIG. 5c, a diagram of a generic triangle 96 is shown. The triangle 96 has three vertices A, B, and C, and three sides of length a, b, and c; and a height h. After calculating an intermediate variable s, where s=(a+b+c)/2, the area of the triangle 96 is given by:

$$\text{Area of Triangle} = \sqrt{[s^*(s-a)(s-b)(s-c)]}, \quad \text{Equation 4}$$

where the symbol "√" denotes a square-root operation. To find the area of the triangle that is bounded by Points E, F, and G, the computer 16 first calculates the intermediate value s, which is given by:

$$s = ((F-E)+(F-G)+(G-E))/2. \quad \text{Equation 5}$$

After the computer 16 calculates the intermediate value s, it determines the area of the triangle by employing Equation 4. The area of the triangle, denoted $A_{triangle\_1}$, that is defined by points E, F, G is the following:

$$A_{triangle\_1} = \sqrt{[s^*(s-(F-E))(s-(F-G))(s-(G-E))]}. \quad \text{Equation 6}$$

The expressions shown in Equations 2, 3, and 6 for the areas of the first and second trapezoids and the triangle are added together to yield the area 93a bounded by points C through H1.

The area 93b, approximated as a triangle bounded by points H1, I and J, can be calculated using Equations 4 and 5. To find the area of the triangle that is bounded by Points H1, I and J, the computer 16 first calculates the intermediate value s, which is given by:

$$s = ((H1-I)+(J-I)+(J-H1))/2. \quad \text{Equation 7}$$

After the computer 16 calculates the intermediate value s, it determines the area of the triangle by employing Equation 4. The area 93b, that is defined by points H1, I, and J is the following:

$$A_{triangle\_2} = \sqrt{[s^*(s-(H1-I))(s-(J-I))(s-(J-H1))]}. \quad \text{Equation 8}$$

The total area 92 calculated is the sum of the area 93a and the area 93b.

A second example of a feature that may be calculated at steps 68 and 70 of process 60 is the peak-to-peak frequency of the waveform segment 90. The peak-to-peak frequency is determined by calculating the duration in time between point F on one beat and point F on the next beat. The range is the frequency of the beat.

A third example of a feature that may be calculated at steps 68 and 70 of process 60 is the baseline-to-peak slope of the waveform segment 90. The slope is determined by calculating the point in time where the waveform 90 starts the ascent at point C to the apex at point F. This difference is referred to as the rise. The quantity of time that the beat takes to reach the apex at point F is referred to as the run. The calculation of the slope is as follows:

$$\text{Slope} = \text{Rise/Run}. \quad \text{Equation 9}$$

A fourth example of a feature that may be calculated at steps 68 and 70 of process 60 is the peak-to-nadir slope of the waveform segment 90. The slope is determined by calculating the point in time where the waveform starts the descent from the apex at point F to the nadir at point I. This difference is referred to as the rise, even though in this case the rise will be a negative number. The quantity of time that the beat takes to reach the nadir at point I is referred to as the run. The calculation of the slope is given above in equation 9.

A fifth example of a feature that may be calculated at steps 68 and 70 of process 60 is the total amplitude of the waveform segment 90. The total amplitude is determined by subtracting the nadir at point I from the apex point at point F. The difference is the value to be considered in the calculation of the total amplitude.

As discussed above, generally, with respect to the scaling step 74 of the comparative process 60, application of the templates to individual patients (e.g., in embodiments in which a transplanted heart is being monitored) is expected to be improved (e.g., is expected to be a more accurate reflection of the condition of tissue) if weighted. Each of the templates, in and of themselves, may provide a less reliable result. The culmination of all of the templates together, however, should better aid in determining the condition of the tissue and the need for intervention. For example, in some embodiments, variations in the templates are not equal indicators of a heart transplant rejection. For example, the variance between baseline and captured templates that are based on the peak-to-peak-frequency calculation may fluctuate simply by the patient being agitated, excited, or stressed. Anything that increases the beats per minute can introduce variance into the template comparison. For this reason, the peak-to-peak frequency template can be considered but may not be the sole determination of heart transplant rejection. A weighting factor may be applied to each of the templates to help balance any abnormalities and thereby increase both the specificity and sensitivity of the results. In some embodiments in which the condition of a tissue (e.g., heart tissue) is monitored, the following weighting factors can be assigned to each of the templates described above with respect to FIGS. 4, and 5a-c:

| | |
|---|---|
| Area Under Curve Template | 50% |
| Peak To Peak Frequency Template | 5% |
| Baseline To Peak Slope Template | 15% |
| Peak To Nadir Slope Template | 15% |
| Total Amplitude Template | 15% |

Various embodiments include methods for assessing a medical condition by carrying out the following steps or at least the following steps: obtaining or providing a first baseline template corresponding to an average of results of a first calculation performed on multiple segments of a first electrical signal acquired at a first time; obtaining or providing a first captured template corresponding to an average of results of the first calculation performed on multiple segments of a second electrical signal acquired a second time later than the first time; obtaining or providing a second baseline template corresponding to an average of results of a second calculation performed on multiple segments of the first electrical signal; obtaining or providing a second captured template corresponding to an average of results of the second calculation performed on multiple segments of the second electrical signal; calculating a first variance between the first baseline and captured templates; calculating a second variance between the second baseline and captured templates; scaling the first and second variances by first and second weighting factors, respectively, to produce first and second scaled variances; and calculating a first sum of the first and second scaled variances.

In an additional step, one can compare the first sum to a threshold value indicative of the medical condition. As noted, the first and second electrical signals can be acquired from first and second electrocardiograms, first and second electromyograms, or first and second electroencephalograms, and the medical condition can be, or can include, heart failure, a neurodegenerative disease, or brain damage. Obtaining a first baseline template can include excluding results of the first calculation that are greater than a first predetermined value (e.g., the sum of a mean and a standard deviation of the results of the first calculation) and that are less than a second predetermined value (e.g., the difference between the mean and the standard deviation) from the average of results of the first calculation. Comparing the first sum to a threshold can include determining that the medical condition exists if the first sum is greater than the threshold. The first and second calculations can be, independently, calculations of an area under a curve, a frequency difference between first and second points each within consecutive segments, an ascending slope from a nadir to an apex, a descending slope from an apex to a nadir, or an amplitude difference between an apex and a nadir.

The methods described above can include one or more of the following additional steps: obtaining or providing a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtaining or providing a third captured template corresponding to an average of results of the third calculation performed on multiple segments of the second electrical signal; obtaining a fourth baseline template corresponding to an average of results of a fourth calculation performed on multiple segments of the first electrical signal, wherein the fourth calculation characterizes a descending slope from an apex to a nadir; obtaining or providing a fourth captured template corresponding to an average of results of the fourth calculation performed on multiple segments of the second electrical signal; obtaining or providing a fifth baseline template corresponding to an average of results of a fifth calculation performed on multiple segments of the first electrical signal, wherein the fifth calculation characterizes an amplitude difference between an apex and a nadir; obtaining or providing a fifth captured template corresponding to an average of results of the fifth calculation performed on multiple segments of the second electrical signal; calculating a third variance between the third baseline and captured templates; calculating a fourth variance between the fourth baseline and captured templates; calculating a fifth variance between the fifth baseline and captured templates; scaling the third, fourth, and fifth variances by third, fourth, and fifth weighting factors, respectively, to produce third, fourth, and fifth scaled variances; calculating a second sum of the first and second scaled variances; calculating a third sum of the first sum and second sums; and comparing the third sum to a threshold value indicative of the medical condition.

One or more of the systems for assessing a medical condition can include at least the following: a registering unit for capturing a first electrical signal at a first time and a second electrical signal at a second time later than the first time; and a controller configured to (a) obtain a first baseline template corresponding to an average of results of a first calculation performed on multiple segments of a first electrical signal acquired at a first time, (b) obtain a first captured template corresponding to an average of results of the first calculation performed on multiple segments of a second electrical signal acquired at a second time later than the first time, (c) obtain a second baseline template corresponding to an average of results of a second calculation performed on multiple segments of the first electrical signal, (d) obtain a second captured template corresponding to an average of results of the second calculation performed on multiple segments of the second electrical signal, (e) calculate a first variance between the first baseline and captured templates, (f) calculate a second variance between the second baseline and captured templates, (g) scale the first and second variances by first and second weighting factors, respectively, to produce first and second scaled variances; and (h) calculate a first sum of the first and second scaled variances.

The controller can be further configured to compare the first sum to a threshold value indicative of the medical condition. The first and second electrical signals can be acquired from first and second electrocardiograms, first and second electromyograms, or first and second electroencephalograms, and the medical condition can be, or can include, heart failure, a neurodegenerative disease, or brain damage. The controller can be further configured to exclude results of the first calculation that are greater than a first predetermined value and that are less than a second predetermined value from the average of results of the first calculation. The first predetermined value can be the sum of a mean and a standard deviation of the results of the first calculation, and the second predetermined value can be the difference between the mean and the standard deviation.

The controller can be further configured to determine that the medical condition exists if the first sum is greater than the threshold. The first and second calculations can be, independently, calculations of an area under a curve, a frequency difference between first and second points each within consecutive segments, an ascending slope from a nadir to an apex, a descending slope from an apex to a nadir, or an amplitude difference between an apex and a nadir.

The systems described above can include a controller that is further configured to: obtain a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtain a third captured template corresponding to an average of results of the third calculation performed on multiple segments of the second electrical signal; obtain a fourth baseline template corresponding to an average of results of a fourth calculation performed on multiple segments of the first electrical signal, wherein the fourth calculation characterizes a descending slope from an apex to a nadir; obtain a fourth captured template corresponding to an average of results of the fourth calculation performed on multiple segments of the second electrical signal; obtain a fifth baseline template corresponding to an average of results of a fifth calculation performed on multiple segments of the first electrical signal, wherein the fifth calculation characterizes an amplitude difference between an apex and a nadir; obtain a fifth captured template corresponding to an average of results of the fifth calculation performed on multiple segments of the second electrical signal; calculate a third variance between the third baseline and captured templates; calculate a fourth variance between the fourth baseline and captured templates; calculate a fifth variance between the fifth baseline and captured templates; scale the third, fourth, and fifth variances by third, fourth, and fifth weighting factors, respectively, to produce third, fourth, and fifth scaled variances; calculate a second sum of the first and second scaled variances; calculate a third sum of the first sum and second sums; and compare the third sum to a threshold value indicative of the medical condition.

The computer program products for assessing a medical condition can be tangibly stored on machine readable media and can include instructions operable to cause one or more processors to: obtain a first baseline template corresponding to an average of results of a first calculation performed on multiple segments of a first electrical signal acquired at a first time; obtain a first captured template corresponding to an average of results of the first calculation performed on multiple segments of a second electrical signal acquired a second time later than the first time; obtain a second baseline template corresponding to an average of results of a second calculation performed on multiple segments of the first electrical signal; obtain a second captured template corresponding to an average of results of the second calculation performed on multiple segments of the second electrical signal; calculate a first variance between the first baseline and captured templates; calculate a second variance between the second baseline and captured templates; scale the first and second variances by first and second weighting factors, respectively, to produce first and second scaled variances; and calculate a first sum of the first and second scaled variances.

The product can further include instructions to compare the first sum to a threshold value indicative of the medical condition. The first and second electrical signals can be acquired from first and second electrocardiograms, first and second electromyograms, or first and second electroencephalograms, and the medical condition can be, or can include, heart failure, a neurodegenerative disease, or brain damage.

The product can further include instructions to obtain a first baseline template comprises excluding results of the first calculation that are greater than a first predetermined value and that are less than a second predetermined value from the average of results of the first calculation. The first predetermined value can be the sum of a mean and a standard deviation of the results of the first calculation and the second predetermined value can be the difference between the mean and the standard deviation. The product can further include instructions to determine that the medical condition exists if the first sum is greater than the threshold. The first and second calculations can be, independently, calculations of an area under a curve, a frequency difference between first and second points each within consecutive segments, an ascending slope from a nadir to an apex, a descending slope from an apex to a nadir, or an amplitude difference between an apex and a nadir.

The product can further include instructions to: obtain a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtain a third captured template corresponding to an average of results of the third calculation performed on multiple segments of the second electrical signal; obtain a fourth baseline template corresponding to an average of results of a fourth calculation performed on multiple segments of the first electrical signal, wherein the fourth calculation characterizes a descending slope from an apex to a nadir; obtain a fourth captured template corresponding to an average of results of the fourth calculation performed on multiple segments of the second electrical signal; obtain a fifth baseline template corresponding to an average of results of a fifth calculation performed on multiple segments of the first electrical signal, wherein the fifth calculation characterizes an amplitude difference between an apex and a nadir; obtain a fifth captured template corresponding to an average of results of the fifth calculation performed on multiple segments of the second electrical signal; calculate a third variance between the third baseline and captured templates; calculate a fourth variance between the fourth baseline and captured templates; calculate a fifth variance between the fifth baseline and captured templates; scaling the third, fourth, and fifth variances by third, fourth, and fifth weighting factors, respectively, to produce third, fourth, and fifth scaled variances; calculate a second sum of the first and second scaled variances; calculate a third sum of the first sum and second sums; and compare the third sum to a threshold value indicative of the medical condition.

A number of embodiments of the invention have been described. Nevertheless, it will be understood that various modifications may be made without departing from the spirit and scope of the invention.

The processes described herein, including comparative process 60, can be implemented in digital electronic circuitry, or in computer software, firmware, or hardware, including the structural means disclosed in this specification and structural equivalents thereof, or in combinations of them. The processes can be implemented as one or more computer program products, i.e., one or more computer programs tangibly embodied in an information carrier, e.g., in a machine readable storage device or in a propagated signal, for execution by, or to control the operation of, data processing apparatus, e.g., a programmable processor, a computer, or multiple computers. A computer program (also known as a program, software, software application, or code) can be written in any form of programming language, including compiled or interpreted languages, and it can be deployed in any form, including as a stand alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes described herein, including method steps, can be performed by one or more programmable processors executing one or more computer programs to perform functions of the processes by operating on input data and generating output. The processes can also be performed by, and apparatus of the processes can be implemented as, special purpose logic circuitry, e.g., an FPGA (field programmable gate array) or an ASIC (application specific integrated circuit).

In some embodiments, the computer 16 may include multiple components selected from the components shown in FIG. 2, including multiple processors. Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of non volatile memory, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

The processes can be implemented in a computing system that includes a back end component (e.g., a data server), a middleware component (e.g., an application server), or a front end component (e.g., a client computer having a graphical user interface or a Web browser through which a user can interact with an implementation of the processes), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

The foregoing are examples for illustration only and not to limit the alternatives in any way. The comparative process 60 and system 10 may be used to assess medical conditions of other tissues, including those from various biological sources, transplanted tissues, tissues generated or modified in tissue culture or cell culture, or that are or that include manmade components, that have not been specifically mentioned above.

Method steps associated with comparative process 60 can be rearranged and/or one or more such steps can be omitted to achieve the same results described herein. Elements of different embodiments described herein may be combined to form other embodiments not specifically set forth above. Accordingly, other embodiments are within the scope of the following claims.

What is claimed is:

1. A method for assessing a medical condition, the method comprising: obtaining a first baseline template corresponding to an average of results of a first calculation performed on multiple segments of a first electrical signal acquired at a first time; obtaining a first captured template corresponding to an average of results of the first calculation performed on multiple segments of a second electrical signal acquired a second time later than the first time; obtaining a second baseline template corresponding to an average of results of a second calculation performed on multiple segments of the first electrical signal; obtaining a second captured template corresponding to an average of results of the second calculation performed on multiple segments of the second electrical signal; calculating a first variance between the first baseline and captured templates; calculating a second variance between the second baseline and captured templates, the first and second variances providing unequal indications of the medical condition; scaling the first and second variances by first and second weighting factors, respectively, to produce first and second scaled variances indicative of the relative importance of the variances; and calculating a first sum of the first and second scaled variances.

2. The method of claim 1, further comprising comparing the first sum to a threshold value indicative of the medical condition.

3. The method of claim 1, wherein the first and second electrical signals are acquired from first and second electrocardiograms; first and second electromyograms; or first and second electroencephalograms.

4. The method of claim 1, wherein the medical condition comprises heart failure; a neurodegenerative disease; or brain damage.

5. The method of claim 1, wherein obtaining a first baseline template comprises excluding results of the first calculation that are greater than a first predetermined value and that are less than a second predetermined value from the average of results of the first calculation.

6. The method of claim 5, wherein the first predetermined value is the sum of a mean and a standard deviation of the results of the first calculation and the second predetermined value is the difference between the mean and the standard deviation.

7. The method of claim 2, wherein comparing the first sum to a threshold further comprises determining that the medical condition exists if the first sum is greater than the threshold.

8. The method of claim 1, wherein the first and second calculations are, independently, calculations of an area under a curve, a frequency difference between first and second points each within consecutive segments, an ascending slope from a nadir to an apex, a descending slope from an apex to a nadir, or an amplitude difference between an apex and a nadir.

9. The method of claim 1, further comprising obtaining a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtaining a third captured template corresponding to an average of results of the third calculation performed on multiple segments of the second electrical signal; obtaining a fourth baseline template corresponding to an average of results of a fourth calculation performed on multiple segments of the first electrical signal, wherein the fourth calculation characterizes a descending slope from an apex to a nadir; obtaining a fourth captured template corresponding to an average of results of the fourth calculation performed on multiple segments of the second electrical signal; obtaining a fifth baseline template corresponding to an average of results of a fifth calculation performed on multiple segments of the first electrical signal, wherein the fifth calculation characterizes an amplitude difference between an apex and a nadir; obtaining a fifth captured template corresponding to an average of results of the fifth calculation performed on multiple segments of the second electrical signal; calculating a third variance between the third baseline and captured templates; calculating a fourth variance between the fourth baseline and captured templates; calculating a fifth variance between the fifth baseline and captured templates; scaling the third, fourth, and fifth variances by third, fourth, and fifth weighting factors, respectively, to produce third, fourth, and fifth scaled variances; calculating a second sum of the third, fourth, and fifth scaled variances; calculating a third sum of the first sum and second sums; and comparing the third sum to a threshold value indicative of the medical condition.

10. A system for assessing a medical condition, the system comprising: a registering unit for capturing a first electrical signal at a first time and a second electrical signal at a second time later than the first time; and a controller configured to: obtain a first baseline template corresponding to an average of results of a first calculation performed on multiple segments of a first electrical signal acquired at a first time; obtain a first captured template corresponding to an average of results of the first calculation performed on multiple segments of a second electrical signal acquired at a second time later than the first time; obtain a second baseline template corresponding to an average of results of a second calculation performed on multiple segments of the first electrical signal; obtain a second captured template corresponding to an average of results of the second calculation performed on multiple segments of the second electrical signal; calculate a first variance between the first baseline and captured templates; calculate a second variance between the second baseline and captured templates, the first and second variances providing unequal indications of the medical condition; scale the first and second variances by first and second weighting factors, respectively, to produce first and second scaled variances indicative of the relative importance of the variances; and calculate a first sum of the first and second scaled variances.

11. The system of claim 10, wherein the controller is further configured to comparing the first sum to a threshold value indicative of the medical condition.

12. The system of claim 10, wherein the first and second electrical signals are acquired from first and second electrocardiograms; first and second electromyograms; or first and second electroencephalograms.

13. The system of claim 10, wherein the medical condition comprises heart failure; a neurodegenerative disease; or brain damage.

14. The system of claim 10, wherein the controller is further configured to exclude results of the first calculation that are greater than a first predetermined value and that are less than a second predetermined value from the average of results of the first calculation.

15. The system of claim 14, wherein the first predetermined value is the sum of a mean and a standard deviation of the results of the first calculation and the second predetermined value is the difference between the mean and the standard deviation.

16. The method of claim 11, wherein the controller is further configured to determine that the medical condition exists if the first sum is greater than the threshold.

17. The system of claim 11, wherein the first and second calculations are, independently, calculations of an area under a curve, a frequency difference between first and second points each within consecutive segments, an ascending slope from a nadir to an apex, a descending slope from an apex to a nadir, or an amplitude difference between an apex and a nadir.

18. The system of claim 11, wherein the controller is further configured to: obtain a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtain a third captured template corresponding to an average of results of the third calculation performed on multiple segments of the second electrical signal; obtain a fourth baseline template corresponding to an average of results of a fourth calculation performed on multiple segments of the first electrical signal, wherein the fourth calculation characterizes a descending slope from an apex to a nadir; obtain a fourth captured template corresponding to an average of results of the fourth calculation performed on multiple segments of the second electrical signal; obtain a fifth baseline template corresponding to an average of results of a fifth calculation performed on multiple segments of the first electrical signal, wherein the fifth calculation characterizes an amplitude difference between an apex and a nadir; obtain a fifth captured template corresponding to an average of results of the fifth calculation performed on multiple segments of the second electrical signal; calculate a third variance between the third baseline and captured templates; calculate a fourth variance between the fourth baseline and captured templates; calculate a fifth variance between the fifth baseline and captured templates; scale the third, fourth, and fifth variances by third, fourth, and fifth weighting factors, respectively, to produce third, fourth, and fifth scaled variances; calculate a second sum of the third, fourth, and fifth scaled variances; calculate a third sum of the first sum and second sums; and compare the third sum to a threshold value indicative of the medical condition.

19. A computer program product for assessing a medical condition, the computer program product being tangibly stored on machine readable media, comprising instructions operable to cause one or more processors to: obtain a first baseline template corresponding to an average of results of a first calculation performed on multiple segments of a first electrical signal acquired at a first time; obtain a first captured template corresponding to an average of results of the first calculation performed on multiple segments of a second electrical signal acquired a second time later than the first time; obtain a second baseline template corresponding to an average of results of a second calculation performed on multiple segments of the first electrical signal; obtain a second captured template corresponding to an average of results of the second calculation performed on multiple segments of the second electrical signal; calculate a first variance between the first baseline and captured templates; calculate a second variance between the second baseline and captured templates, the first and second variances providing unequal indications of the medical condition; scaling the first and second variances by first and second weighting factors, respectively, to produce first and second scaled variances indicative of the relative importance of the variances; and calculate a first sum of the first and second scaled variances.

20. The product of claim 19, further comprising instructions to compare the first sum to a threshold value indicative of the medical condition.

21. The product of claim 19, wherein the first and second electrical signals are acquired from first and second electrocardiograms; first and second electromyograms; or first and second electroencephalograms.

22. The product of claim 19, wherein the medical condition comprises heart failure; a neurodegenerative disease; or brain damage.

23. The product of claim 19, further comprising instructions to obtain a first baseline template comprises excluding results of the first calculation that are greater than
  a first predetermined value and that are less than a second predetermined value from the average of results of the first calculation.

24. The product of claim 23, wherein the first predetermined value is the sum of a mean and a standard deviation of the results of the first calculation and the second predetermined value is the difference between the mean and the standard deviation.

25. The product of claim 20, further comprising instructions to determine that the medical condition exists if the first sum is greater than the threshold.

26. The product of claim 19, wherein the first and second calculations are, independently, calculations of an area under a curve, a frequency difference between first and second points each within consecutive segments, an ascending slope from a nadir to an apex, a descending slope from an apex to a nadir, or an amplitude difference between an apex and a nadir.

27. The product of claim 19, further comprising instructions to: obtain a third baseline template corresponding to an average of results of a third calculation performed on multiple segments of the first electrical signal, wherein the first calculation characterizes an area under a curve, the second calculation characterizes a frequency difference between first and second points each within consecutive segments, and the third calculation characterizes an ascending slope from a nadir to an apex; obtain a third captured template corresponding to an average of results of the third calculation performed on multiple segments of the second electrical signal; obtain a fourth baseline template corresponding to an average of results of a fourth calculation performed on multiple segments of the first electrical signal, wherein the fourth calculation characterizes a descending slope from an apex to a nadir; obtain a fourth captured template corresponding to an average of results of the fourth calculation performed on multiple segments of the second electrical signal; obtain a fifth baseline template corresponding to an average of results of a fifth calculation performed on multiple segments of the first electrical signal, wherein the fifth calculation characterizes an amplitude difference between an apex and a nadir; obtain a fifth captured template corresponding to an average of results of the fifth calculation performed on multiple segments of the second electrical signal; calculate a third variance between the third baseline and captured templates; calculate a fourth variance between the fourth baseline and captured templates; calculate a fifth variance between the fifth baseline and captured templates; scaling the third, fourth, and fifth variances by third, fourth, and fifth weighting factors, respectively, to produce third, fourth, and fifth scaled variances; calculate a second sum of the third, fourth, and fifth scaled variances; calculate a third sum of the first sum and second sums; and compare the third sum to a threshold value indicative of the medical condition.

* * * * *